Nov. 16, 1954
O. H. VARDEN
Plant Pat. 1,322
PYRACANTHA PLANT
Filed Feb. 5, 1954
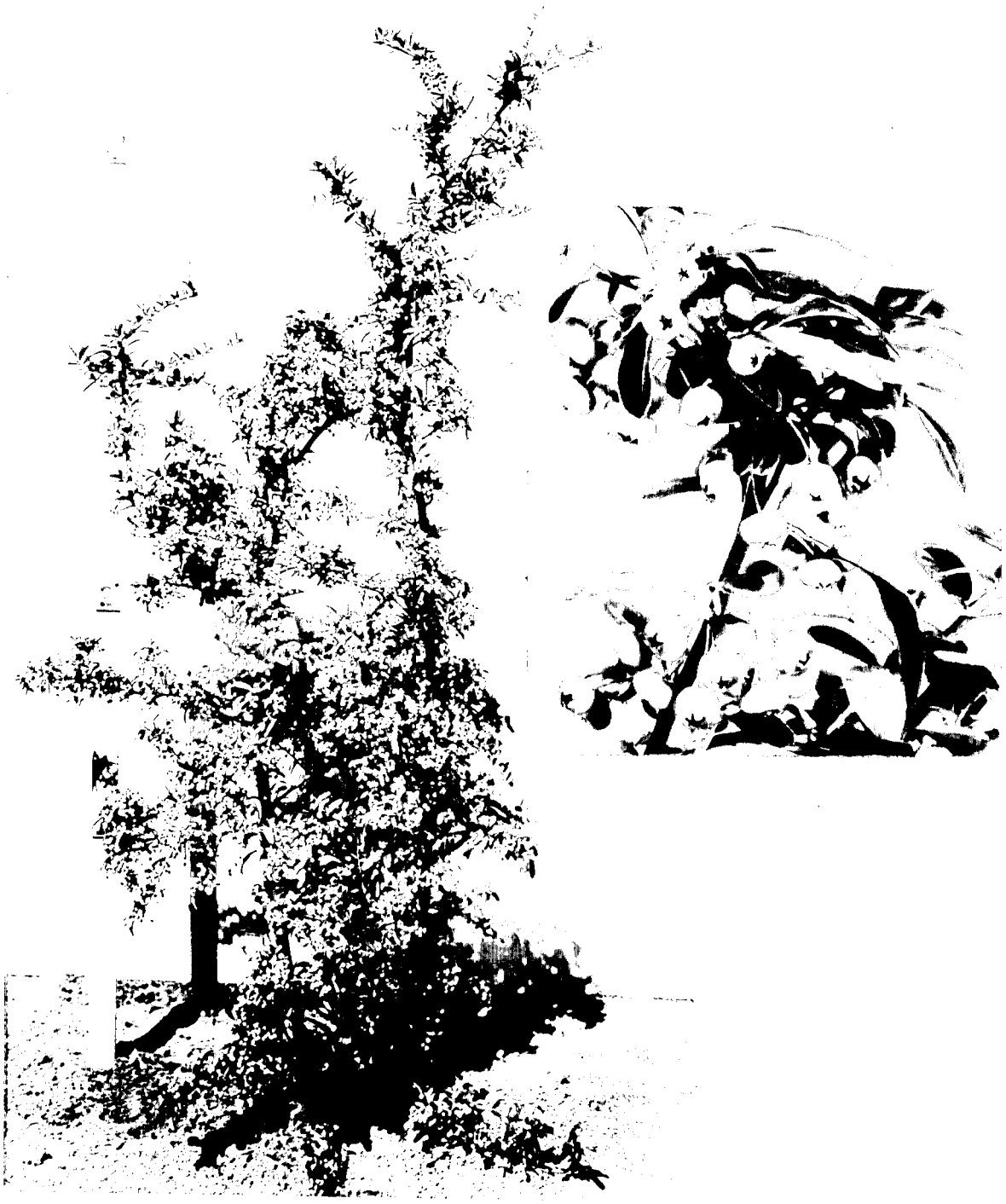
Inventor.
O. H. Varden
By: Robb & Robb
Attorneys.

United States Patent Office

Plant Pat. 1,322
Patented Nov. 16, 1954

1,322

PYRACANTHA PLANT

Owen H. Varden, East Rutherford, N. J., assignor to Bobbink Nurseries, Inc., East Rutherford, N. J., a corporation of New Jersey Application February 5, 1954, Serial No. 408,631

1 Claim. (Cl. 47—59)

The present invention relates to a new and distinct variety of pyracantha plant, commonly called "Firethorn," which was produced by me as the result of a planned crossing of two unpatented varieties known as "Coccinea" and "Coccinea Lalandi."

The primary objective in making this cross was to produce a new variety of pyracantha plant having improved ornamental characteristics, combined with hardiness at least as good as the hardiest pyracantha varieties formerly available in commerce. This objective was fully achieved by selecting from the 38 seedlings resulting from the aforementioned cross, a single seedling which was characterized by an abundance and unique coloring of its fruit by its compact and rich dark green foliage, combined with excellent hardiness. This combination of characteristics definitely distinguishes my new variety from its parents, as well as from all others of its class.

My new variety is endowed with a hardiness equal to that of "Coccinea," and the color of the fruit of my new variety is more highly ornamental and more attractive than that of "Coccinea Lalandi." The distinctive scarlet red general color tonality of the fruit of my new variety, and the abundance of said fruit, are not found in any other variety which is hardy without special protective precautions in Zones 5 and 6 of the Hardiness Map as published in the Atlas of American Agriculture by the U. S. Department of Agriculture, at Washington, D. C., in 1936.

Asexual reproduction of my new variety by cuttings, as performed by me at East Rutherford, New Jersey, shows that the foregoing characteristics and distinctions come true to form and are established and transmitted through succeeding propagations.

The accompanying drawing shows in black-and-white a typical specimen plant of my new pyracantha variety as associated with a height scale marked in feet, and also shows on a somewhat enlarged scale and in full color a detailed view of some of the fruit and foliage, with the colors depicted as nearly true as it is reasonably possible to make the same in a color illustration of this character.

The following is a detailed description of my new variety, with color terminology in accordance with Ridgway's Color Standards and Nomenclature:

Type: Hardy; outdoor seedling; ornamental broad leaf evergreen; for ornamental garden planting.

Class: Hybrid Coccinea.

Breeding: Seedling.

*Seed parent.*—"Coccinea Lalandi."

*Pollen parent.*—"Coccinea."

Location where described specimens were grown: East Rutherford, New Jersey.

Habit of growth: Primarily upright, with some tendency to spread.

Branches: Irregular; thorny.

Foliage:

*Leaflets.*—Shape—oval, with apex acuately blunt. Base—imperfectly oval. Margin—obsoletely serrate.

*Leaves.*—Alternate; pinnately compound; varying from 3 to 5 in number; moderate abundant; moderately small; leathery; semi-glossy.

*Color.*—Mature: upper surface—Yew Green, Plate XXXI, 27, m; under surface—Cress Green, Plate XXXI, 29, k. Young: upper surface—Light Cress Green, Plate XXXI, 29, i; under surface—Absinthe Green, Plate XXXI, 29, —.

Stem:

*New growth.* — Total surface — color — Absinthe Green, Plate XXXI, 29, —.

*Old growth (1-year old).*—Color: upper surface—Saccardo's Olive, Plate XVI, 19, m; under surface—Light Cress Green, Plate XXXI, 29, i.

*Thorns.*—Many; medium size; straight; with short, round base.

Trunk (3-year old growth): Total surface—Color—Olive Brown, Plate XL, 17, k.

Flowers: Compound corymbs consisting of 15 florets; each corymb about 1½ inches broad; size of individual floret when fully open very small, approximately 3/16 inch.

*Petalage.*—Single; arranged regularly; 5 petals; flat, with slight cupping; thin; satiny. Color: outside surface—from White to Pale Olive Buff, Plate XL, 21, f; inside surface—from White to Yellowish Glaucous, Plate XLI, 25, f.

*Stamens.*—20 in number; arranged regularly about pistils.

*Filaments.*—Long; with anthers. Color—yellowish.

*Anthers.*—Small; all open at once. Color—Buckthorn Brown, Plate XV, 17, i.

*Pollen.*—Very abundant. Color—Primuline Yellow, Plate XVI, 19, —.

*Pistils.*—Few.

Fruit: Globular pome, with persistent calyx; approximately 3/8 inch in diameter. Color: outside surface—from Scarlet Red, Plate I, 3, — to Nopal Red, Plate I, 3, i; inside surface—Pale Orange Yellow, Plate III, 17, f.

Seeds: Uusally 5; 3/32 inch long; small. Color—blackish brown (1), Plate XLV, 1, m.

Disease resistance: Highly resistant to usual diseases to which ornamental plants are normally subject, as determined by comparison with other varieties grown under comparable cultural conditions at East Rutherford, New Jersey.

Hardiness: Hardy without any protection, particularly in Zones 5 and 6 of the Hardiness Map published in the Atlas of American Agriculture hereinbefore identified.

I claim:

A new and distinct variety of pyracantha plant of the hybrid Coccinea class, substantially as herein shown and described, characterized particularly as to novelty by the abundance and the scarlet red general color tonality of its fruit, by its compact and rich dark green foliage, and by its hardiness.

No references cited.